United States Patent [19] [11] 4,198,527
Henrick [45] Apr. 15, 1980

[54] ETHER SUBSTITUTED CYCLOPROPANECARBOXYLIC ACIDS AND ESTERS

[75] Inventor: Clive A. Henrick, Palo Alto, Calif.

[73] Assignee: Zoecon Corporation, Palo Alto, Calif.

[21] Appl. No.: 942,509

[22] Filed: Sep. 15, 1978

[51] Int. Cl.$^2$ .................. C07C 61/04; C07C 69/74
[52] U.S. Cl. ...................... 562/506; 260/340.5 R; 260/347.4; 260/465 D; 260/544 D; 260/544 L; 424/304; 424/308; 560/17; 560/61; 560/62; 560/124; 562/431; 562/471; 562/472; 549/76; 549/77; 549/79; 424/305
[58] Field of Search .................. 562/431, 471, 506; 560/17, 61, 124

[56] References Cited

U.S. PATENT DOCUMENTS

| | | | |
|---|---|---|---|
| 3,156,725 | 11/1964 | Kaiser et al. | 562/431 |
| 4,024,163 | 5/1977 | Elliott et al. | 562/506 |
| 4,056,628 | 11/1977 | Winternitz | 424/308 |

OTHER PUBLICATIONS

Julia et al., Chemical Abstracts, vol. 64, 19463–19465 (1966).
Wenkert et al., J. Am. Chem. Soc., vol. 92, pp. 7428–7436 (1970).
Ando et al., J. Org. Chem., vol. 42, pp. 3365–3372 (1977).

Primary Examiner—Dolph H. Torrence
Attorney, Agent, or Firm—Donald W. Erickson

[57] ABSTRACT

Novel esters of ether and thioether substituted cyclopropanecarboxylic acids, synthesis thereof, and intermediates therefor, such esters being useful as pesticides.

11 Claims, No Drawings

ETHER SUBSTITUTED CYCLOPROPANECARBOXYLIC ACIDS AND ESTERS

This invention relates to novel esters of substituted cyclopropane carboxylic acid, synthesis thereof and intermediates therefor, such esters being useful as pesticides.

The novel compounds of the present invention are represented by the following generic formula (A):

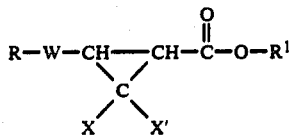

wherein,
W is oxygen or sulfur;
X is lower alkyl or halogen;
X' is hydrogen, lower alkyl or halogen;
R is lower alkyl, lower haloalkyl, lower alkenyl, lower haloalkenyl, or the group

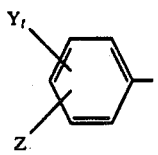

in which,
t is zero, one, two, three or four;
Y is independently selected from hydrogen, lower alkyl, lower haloalkyl, lower alkoxy, lower alkylthio, lower alkylcarbonyl, lower alkoxycarbonyl, lower aryloxy, halogen, cyano, nitro and lower haloalkylthio;
Z is independently selected from the values of Y, cycloalkyl, and lower haloalkoxy; or together with Y forms a methylenedioxy group; and
$R^1$ is the group

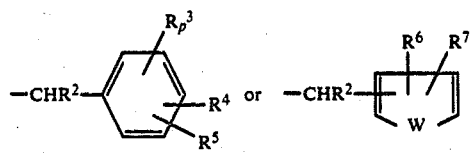

in which,
p is zero, one, two or three;
$R^2$ is hydrogen, cyano, methyl or ethynyl;
$R^3$ is halogen, lower alkyl, lower haloalkyl, lower alkoxy, lower haloalkoxy, lower alkylthio, lower alkenyl, or lower haloalkenyl;
$R^4$ is hydrogen or together with $R^3$ forms a lower alkyl-enedioxy bridge across adjacent ring carbon atoms;
$R^5$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;
$R^6$ is hydrogen or lower alkyl; and
$R^7$ is lower alkenyl, lower alkynyl, or aralkyl.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of R through $R^7$, W, X, X', Y, Z, p and t is as defined hereinabove, unless otherwise specified.

The compounds of formula (A) can be prepared by the reaction of an acid of formula I or the acid halide thereof with an alcohol ($R^1$—OH). For example, the acid I is reacted with thionyl chloride in the presence of a solvent such as hexamethylphosphoric triamide (HMPT), dimethylformamide (DMF), tetrahydrofuran (THF) and the like, and then with the alcohol $R^1$—OH in the presence of a catalyst such as 4-dimethylaminopyridine.

Alternatively, an acid of formula (I) is reacted with the halide, e.g. bromide, or mesylate corresponding to the alcohol $R^1$—OH, in the presence of a base such as potassium carbonate and the like in an organic solvent to prepare the esters of formula A.

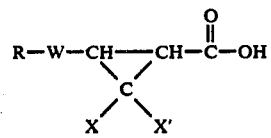

Acids of formula I wherein X is lower alkyl and X' is hydrogen or lower alkyl can be synthesized by the reaction of a vinyl ether or vinyl thioether of formula II with ethyl diazoacetate, either neat or in the presence of a catalyst such as copper or cupric sulfate, to form the ethyl ester III. Cf. *Bull. Soc. Chem. I*, 185 (1956). The ester III is then hydrolyzed to form the acid I.

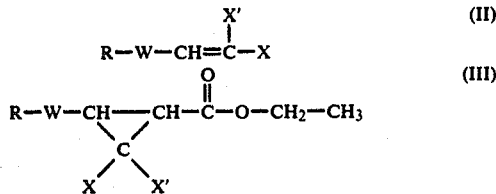

The compounds of formula II wherein W is oxygen, X is lower alkyl and X' is hydrogen or lower alkyl can be synthesized by the reaction of an alcohol R—OH with an appropriately alkyl-substituted allylic halide such as 3-chloro-2-methyl-1-propene, in the presence of a base such as potassium carbonate in a suitable solvent. The resultant compound of formula IV is then rearranged by reaction with potassium t-butoxide or by reaction with a catalyst such as rhodium tristriphenylphosphine chloride to give the vinyl ethers of formula II. Cf. *J. Am. Chem. Soc.* 83, 1701 (1961) and *J. Org. Chem.* 38, 3224 (1973).

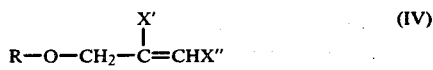

The vinyl thioethers of formula II (W is sulfur, X' is hydrogen or lower alkyl, X" is hydrogen or lower alkyl of one to five) can be synthesized by the reaction of R—SH, in the presence of a catalyst, or of (CH$_3$)$_3$SiCH-(Li)SR with an aldehyde such as 2-methyl-1-propanal. Cf. *J. Org. Chem.* 40, 812 (1975), ibid. 37, 939 (1972), and *Chemistry Letters (Japan)*, 479 (1973).

Compounds of formula III wherein each of X and X' is halogen can be made by the reaction of ethyl propiolate with either a thiol R—SH or an alcohol R—OH to prepare an ester of formula V which is then reacted with phenyl (trihalomethyl) mercury or the like to give the ester III. Cf. *Accounts of Chemical Research* 5, 65 (1972), *Int. J. Sulfur Chem.* 8, 205 (1973), and *Bull. Soc. Chem.* France, 2005 (1974). Alternatively, dihalocarbene can be generated from ethyl trichloroacetate or sodium trichloroacetate.

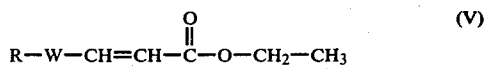

The following terms, whereever used in the description herein and the appended claims, have the meaning defined below unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to a ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to six carbon atoms. The term "lower haloalkenyloxy" refers to a lower alkenyloxy group substituted with one to three halogen atoms.

The term "lower alkynyl" refers to a alkynyl group, straight or branched, having a chain length of two to six carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to six carbon atoms.

The term "cycloalkyl" refers to a cycloalkyl group of three to six cyclic carbon atoms. The term "cycloalkalkyl" refers to a cycloalkyl group wherein one hydrogen atom is replaced by a lower alkyl group, the total number of carbon atoms being from four to eight, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, lower alkylthio, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula (A) are useful pest control agents, particularly for the control of insects and acarids. In the use of the compounds of formula (A) for combatting insects and acarids for the protection of agricultural crops, for example soybeans, cotton, alfalfa, etc., a compound of formula (A), or mixtures thereof, together with a carrier is applied to the locus in a pesticidally effective amount. The carrier can be liquid or solid and include adjuvants such as wetting agents, dispersing agents and other surface active ingredients. The compounds of formula (A) can be used in formulations such as wettable powders, solutions, dusts, granules emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) in the formulation can vary widely, generally within the range of about 0.01 percent to about 90.0 percent, by weight.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

A. A mixture of 4-chlorophenol (10 g, 0.078 mol) and potassium carbonate (32.25 g, 0.233 mol) in 20 ml DMF is stirred for 30 min at 25°. 1.1 Equivalents of 3-chloro-2-methyl-1-propene in 10 ml DMF is added dropwise at 0° and the mixture is allowed to warm to RT. After stirring at RT for 19 hr, the reaction is checked by thin layer chromatography (TLC) developing with 30% ethyl acetate/hexane. As some starting alcohol is still present, another 0.5 equivalent of 3-chloro-2-methyl-1-propene is added (a total of 1.6 equivalents) and the reaction mixture is heated at 50° for 7 hr. The reaction product is worked up with ice water and ether. The organic phase is washed with 5% NaOH, water until neutral, brine, and dried over magnesium sulfate and solvent is removed to give 3-(4-chlorophenoxy)-2-methyl-1-propene.

Seven grams of 3-(4-chlorophenoxy)2-methyl-1-propene and 0.35 g of potassium t-butoxide are heated at 150° under nitrogen for 3 days. The mixture is then worked up with water and extracted with ether. The organic phase is washed with dilute acid, water and brine, dried over magnesium sulfate and solvent is removed to yield 3-(4-chlorophenoxy)-2-methyl-2-propene.

B. A mixture of 3-(4-chlorophenoxy)-2-methyl-2-propene (4.5 g, 0.032 mol) and 0.158 g of copper powder is heated at 110° for 30 min; then 2.78 g ethyl diazoacetate (0.025 mol) is added dropwise, keeping the temperature at 110°. After the addition is complete (approximately 30 min), the mixture is stirred at 110° until nitrogen evolution is complete. The mixture is cooled, diluted with ether, filtered and concentrated. Distillation of the residue yields ethyl 3-(4-chlorophenoxy)-2,2-dimethylcyclopropanecarboxylate.

The ethyl 3-(4-chlorophenoxy)-2,2-dimethylcyclopropanecarboxylate (1.5 g) is hydrolyzed by heating under reflux with 10% potassium hydroxide in a mixture of 20% water and 80% ethyl alcohol for 1 hr and letting stand at 25° overnight. The solution is cooled and solvent is removed in vacuo. The residue is diluted with water and extracted with ether. The aqueous phase is then acidified with aqueous HCl and extracted with ether. The organic phase is washed with water and brine, dried over sodium sulfate and the solvent removed in vacuo to give 3-(4-chlorophenoxy)-2,2-dimethylcyclopropanecarboxylic acid.

C. A mixture of 3-(4-chlorophenoxy)-2,2-dimethylcyclopropanecarboxylic acid (0.95 g, 3,95 mmol), thionyl chloride (0.342 ml, 4.74 mmol) and DMF (several drops) in 50 ml benzene is stirred at RT for 2 days. The solvent and excess thionyl chloride are evaporated under reduced pressure. The resulting acid chloride is dissolved in 50 ml benzene, and 0.79 g m-phenoxybenzyl alcohol (3.95 mmol) and 0.482 g 4-dimethylaminopyridine (3.95 mmol) are added. The mixture is left at 25° for 18 hr and then heated under reflux for 2 hr. The mixture is then poured into water and extracted with ether. The organic phase is washed with dilute HCl, sat.NaHC$_3$, water and brine, dried and concentrated under vacuum. The crude product is purified by preparative TLC developing with 20% ethyl acetate/hexane to yield m-phenoxybenzyl 3-(4-chlorophenoxy)-2,2-dimethylcyclopropanecarboxylate, MS m/e 422 [M+].

EXAMPLE 2

A. A mixture of 4chlorophenol (10 g, 0.78 mol) and sodium hydride (1.9 g, 0.08 mol) is heated to reflux for 30 min in 30 ml of THF and then cooled. 3-Chloro-2-methyl-1-propene (7.3 g, 0.08 mol) in 10 ml THF is added and the mixture is heated to reflux. After 24 hr, an additional equivalent of 3-chloro-2-methyl-1-propene is added and the mixture heated under reflux for another 24 hr. The reaction mixture is cooled and diluted with ether to 150 ml, washed with 20% NaOH (2X) and with water until neutral, then dried and solvent is removed to yield 3-(4-chloro-phenoxy)-2-methyl-1-propene.

The 3-(4-chlorophenoxy)-2-methyl-1-propene (10.2 g) and 0.5 g potassium t-butoxide are stirred together neat at 150° for 18 hr. The reaction is then cooled, another 0.5 g of potassium 5-butoxide is added and the mixture heated at 150° for 4 days. The reaction is diluted with ether, washed with water, dried and solvent is removed to give 3-(4-chlorophenoxy)-2-methyl-2

Following the procedure of Example 1B, 7.2 g (0.040 mol) of 3-(4-chlorophenoxy)-2-methyl-2-propene and 0.2 g copper powder are reacted with 8.7 g (0.079 mol) ethyl diazoacetate to yeild ethyl 3-(4-chlorophenoxy)-2,2-dimethylcyclopropanecarboxylate, which is then hydrolyzed to give 3-(4-chlorophenoxy)-2,2-dimethylcyclopropanecarboxylic acid.

B. The cyanohydrin of m-phenoxybenzaldehyde (8.5 g, 0.038 mol) is dissolved in 150 ml ether and cooled to 0° in an ice bath. To this is slowly added methanesulfonyl chloride in 20 ml ether. The mixture is stirred for 10 min, then triethylamine in 20 ml ether is added dropwise. The solution turns white, and a precipitate appears. The reaction mixture is kept at 0° overnight and is then worked up with water and extracted with ether. The ether phase is washed with 30% sodium bisulfite solution (2X), ether and water (2X), and dried over sodium sulfate. The mixture is filtered and the filtrate concentrated to give α-cyano-m-phenoxybenzyl methanesulfonate.

The 3-(4-chlorophenoxy)-2,2-dimethylcyclopropanecarboxylic acid (0.82 g, 3.40 mmol) from A above is stirred together with 0.34 g (3.40 mmol) potassium bicarbonate in 10 ml THF/DMF (1:1) for 15 min. Then 1.0 g (3.40 mmol) α-cyano-m-phenoxybenzyl methanosulfonate in 5 ml THF/DMF (1:1) is added and the mixture stirred for approx. 48 hr. The reaction is diluted with ether, washed with water (3X) and sat. NaC, dried and solvent is removed. The crude product is purified by prep. TLC developing with 10% ethyl acetate/hexane to yeild α-cyano-m-phenoxybenzyl 3-(4-chlorophenoxy)-2,2-dimethylcyclopropanecarboxylate, which separates into two compounds, the lower band believed to be the cis isomer [compound 2a, MS m/e 447 (M+)] and the upper band believed to be the trans isomer [compound 2b, MS m/e 447 (M+)].

EXAMPLE 3

A. In 100 ml DMF is placed 2,2,2-trifluoroethanol (20 g), 3-chloro-2-methyl-1-propene (18.1 g) and potassium carbonate (33.15 g). The mixture is heated to 50°, with stirring, for 15 hr. The solution is cooled and extracted with pentane. The pentane layer is washed with water (3X) and dried over sodium sulfate. The pentane is fractionally distilled off and the product is distilled in vacuo to give 2,2,2-trifluoroethyl 2-methyl-2-propenyl ether.

In 100 ml 20% ethanol/water is added 11 g (71.4 mmol) 2,2,2-trifluoroethyl 2-methyl-2-propenyl ether and 0.59 g (0.642 mmol) 1,4-diazobicyclo(2,2,2)octane. Rhodium tris-triphenylphosphine chloride (16 g, 142.8 mmol) is then added to the stirring mixture, and the solution is heated to 90° for 4 hr. The reaction is then cooled, brought up in pentane, filtered, washed with water and brine and dried over sodium sulfate. The crude product is distilled, yielding 2,2,2-trifluoroethyl 2-methyl-1-propenyl ether.

2,2,2-Trifluoroethyl 2-methyl-1-propenyl ether (3.2 g) is combined, under nitrogen, with approx. 150 mg copper powder and heated to 130°. Ethyl diazoacetate (2.36 g) is very slowly added to the solution over 1.5 hr. The solution is then cooled and filtered, and the filtrate is washed with ether. The ether phase is distilled in vacuo to yield ethyl 3-(2,2,2-trifluoroethoxy)-2,2-dimethylcyclopropanecarboxylate.

The above product (1.3 g, 5.41 mmol) is combined with potassium hydroxide (0.455 g, 8.11 mmol) in ethanol/water (5:1) and heated under reflux for 2 hr. The solution is cooled and the ethanol is removed in vacuo. The residue is treated with 10% aqueous NaOH and extracted with ether. The aqueous layer is acidified with 10% HC and extracted with ether. The ether phase is washed with water and brine, dried over sodium sulfate, and the solvent removed in vacuo, yielding 3-(2,2,2-trifluoroethoxy)-2,2-dimethylcyclopropanecarboxylic acid.

B. To 10 ml DMF is added 0.88 g 3-(2,2,2-trifluoroethoxy)-2,2-dimethylcyclopropanecarboxylic acid (4.14 mmol) and 1.146 g potassium carbonate (8.29 mmol), after which is added 12 g m-phenoxybenzyl bromide. This mixture is stirred under nitrogen for 15 hr. The reaction mixture is extracted with ether and the ether phase is washed with water (3X) and brine, and dried over sodium sulfate. The solvent is then removed to yield m-phenoxybenzyl 3-(2,2,2-trifluoroethoxy)-2,2-dimethylcyclopropanecarboxylate, MS m/e 394.1 (M+).

EXAMPLE 4

Following the procedure of Example 1, each of 4-t-butylphenol and 4-cresol is reacted with 3-chloro-2-methyl-1-propene, then potassium t-butoxide and finally ethyl diazoacetate followed by hydrolysis, to give, respectively, 3-(4-t-butyl-phenoxy)-2,2-dimethylcyclopropanecarboxylic acid and 3-(4-methylphenoxy)-2,2-dimethylcyclopropanecarboxylic acid.

The 3-(4-t-butylphenoxy)-2,2-dimethylcyclopropanecarboxylic acid and the 3-(4-methylphenoxy)-2,2-dimethylcyclopropanecarboxylic acid is each reacted with thionyl chloride and then with m-phenoxybenzyl alcohol to yield, respectively, m-phenoxybenzyl 3-(4-t-butylphenoxy)-2,2-dimethylcyclopropanecarboxylate [MS m/e 444 (M+)] and m-phenoxybenzyl 3-(4-methylphenoxy)-2,2-dimethylcyclopropanecarboxylate [MS m/e 402 (M+)].

EXAMPLE 5

Following the procedure of either Example 1 or 2, the alcohols of column I are reacted to produce the acids of column II.

I 4-chloro-2-fluorophenol
2-trifluoromethylphenol
4-trifluoromethylphenol
2-fluorophenol
2,4-difluorophenol
2-chlorophenol
2-cresol
2- chloro-4-methylphenol p0 4- chloro-2-nitrophenol
2-fluoro-4-trifluoropheno
4-bromo-2-chlorophenol

II 3-(4-chloro-2-fluorophenoxy)-2,2-dimethylcyclopropanecarboxylic acid
3-(2-trifluoromethylphenoxy)-2,2-dimethylcyclopropanecarboxylic acid
3-(-b 4-trifluoromethylphenoxy)-2,2-dimethylcyclopropanecarboxylic acid
3-(2-fluorophenoxy)-2,2-dimethylcyclopropanecarboxylic acid
3-(2,4-difluorophenoxy)-2,2-dimethylcyclopropanecarboxylic acid
3-(2-chlorophenoxy)-2,2-dimethylcyclopropanecarboxylic acid
3-(2-methylphenoxy)-2,2-dimethylcyclopropanecarboxylic acid
3-(2-chloro-4-methylphenoxy)-2,2-dimethylcyclopropanecarboxylic acid
3-(4-chloro-2-nitrophenoxy)-2,2-dimethylcyclopropanecarboxylic acid
3-(2-fluoro-4-trifluoromethylphenoxy)-2,2-dimethylcyclopropanecarboxylic acid
3-(4-bromo-2-chlorophenoxy)-2,2-dimethylcyclopropanecarboxylic acid

EXAMPLE 6

Each of the carboxylic acid intermediates listed under column II is reacted with m-phenoxybenzyl bromide using the procedure of Example 3B to yield the respective ester under column III.

III m-phenoxybenzyl 3-(4-chloro-2-fluorophenoxy)-2,2-dimethylcyclopropanecarboxylate
m-phenoxybenzyl 3-(2-trifluoromethylphenoxy)-2,2-dimethylcyclopropanecarboxylate
m-phenoxybenzyl 3-(4-trifluoromethylphenoxy)-2,2-dimethylcyclopropanecarboxylate
m-phenoxybenzyl 3-(2-fluorophenoxy)-2,2-dimethylcyclopropanecarboxylate
m-phenoxybenzyl 3-(2,4-difluorophenoxy)-2,2-dimethylcyclopropanecarboxylate
m-phenoxybenzyl 3-(2-chlorophenoxy)-2,2-dimethylcyclopropanecarboxylate
m-phenoxybenzyl 3-(2-methylphenoxy)-2,2-dimethylcyclopropanecarboxylate
m-phenoxybenzyl 3-(2-chloro-4-methylphenoxy)-3,3-dimethylcyclopropanecarboxylate
m-phenoxybenzyl 3-(4-chloro-2-nitrophenoxy)-2,2-dimethylcyclopropanecarboxylate
m-phenoxybenzyl 3-(2-fluoro-4-trifluoromethylphenoxy)-2,2-dimethylcyclopropanecarboxylate
m-phenoxybenzyl 3-(4-bromo-2-chlorophenoxy)-2,2-dimethylcyclopropanecarboxylate

EXAMPLE 7

Following the procedure of Example 2, 3-(4-methylphenoxy)-2,2-dimethylcyclopropanecarboxylic acid is prepared from 4-cresol, which is then reacted with α-cyano-m-phenoxybezyl methanesulfonate to yield α-cyano-m-phenoxybezyl 3-(4-methylphenoxy)-2,2-dimethylcyclopropanecarboxylate.

EXAMPLE 8

Following the procedure of Example 2B, each of the acids listed under column II is reacted with α-cyano-m-phenoxybenzyl methanesulfonate to yield the respective esters in column IV.

IV

α-cyano-m-phenoxybenzyl 3-(4-chloro-2-fluorophenoxy)-2,2-dimethylcyclopropanecarboxylate
α-cyano-m-phenoxybenzyl 3-(-b 2-trifluoromethylphenoxy)-2,2-dimethylcyclopropanecarboxylate
α-cyano-m-phenoxybenzyl 3-(4-trifluoromethylphenoxy)-2,2-dimethylcyclopropanecarboxylate
α-cyano-m-phenoxybenzyl 3-(2-fluorophenoxy)-2,2-dimethylcyclopropanecarboxylate α-cyano-m-phenoxybenzyl 3-(2,4-difluorophenoxy)-2,2-dimethylcyclopropanecarboxylate
α-cyano-m-phenoxybenzyl 3-(-b 2-chlorophenoxy)-2,2-dimethylcyclopropanecarboxylate
α-cyano-m-phenoxybenzyl 3-(2-methylphenoxy)-2,2-dimethylcyclopropanecarboxylate
α-cyano-m-phenoxybenzyl 3-(2-chloro-3-methylphenoxy)-2,2-dimethylcyclopropanecarboxylate
α-cyano-m-phenoxybenzyl 3-(4-chloro-2-nitrophenoxy)-2,2-dimethylcyclopropanecarboxylate
α-cyano-m-phenoxybenzyl 3-(2-fluoro-4-trifluoromethylphenoxy)-2,2-dimethylcyclopropanecarboxylate
α-cyano-m-phenoxybenzyl 3-(4-bromo-2-chlorophenoxy)-2,2-dimethylcyclopropanecarboxylate

EXAMPLE 9

To a mixture of 3-(4-chlorophenoxy)-2,2-dimethylcyclopropanecarboxylic acid (2.77 mmol) (as prepared in, for example, Example 1 or 2), potassium carbonate (3.25 mmol) and hexamethylphosphoric triamide (HMPT) (3 ml), with stirring and under nitrogen, at RT, is added 5-benzyl-3-furylmethyl bromide (2.77 mmol) in THF. The reaction is stirred at RT for about 48 hr and then worked up by partition between water/ether. The organic phase is washed with water and brine, dried over potassium carbonate, filtered and the solvent is removed from the filtrate. The residue is plated on prep. TLC plates developing with 10% ether/hexane to yield 5-benzyl-3-furylmethyl 3-(4-chlorophenoxy)-2,2-dimethylcyclopropanecarboxylate.

EXAMPLE 10

Following the method of Example 3, each of the acids of column V is formed from its respective alcohol (R—OH).

V 3-propoxy-2,2-dimethylcyclopropanecarboxylic acid
3-but-2-enoxy-2,2-dimethylcyclopropanecarboxylic acid
3-(3-fluoropropenoxy)-2,2-dimethylcyclopropanecarboxylic acid
3-(t-butoxy)-2,2-dimethylcyclopropanecarboxylic acid
3-(4-chloro-3-fluorobut-3-enoxy)-2,2-dimethylcyclopropanecarboxylic acid Each of the compounds in column V is then reacted with m-phenoxybenzyl bromide, as in Example 3, to yield the m-phenoxybenzyl ester (column VI). m-pheoxybenzyl 3-propoxy 2,2-dimethylcyclopropanecarboxlate
m-phenoxybenzyl 3-but-2l -enoxy-2,2-dimethylcyclopropanecarboxylate
m-phenoxybezyl 3-(3-fluoropropenoxy)-2,2-dimethylcyclopropanecarboxylate
m-phenoxybenzyl 3-(t-butoxy)-2,2-dimethylcyclopropanecarboxylate
m-phenoxybenzyl 3-(4-chloro-3-fluorobut-2-enoxy)-2,2-dimethylccycloprpanecarboxylate

EXAMPLE 11

Following the procedure of Example 9, 3-(4-fluorophenoxy)-2,2-dimethylcyclopropanecarboxylic acid is reacted with each of m-allyloxybenzyl bromide, m-propargyloxybenzyl bromide and m-(o-fluorophenoxy)-benzyl bromide to yield, respectively m-allyloxybenzyl 3-(4-fluorophenoxy)-2,2-dimethylcyclopropanecarboxylate, m-propargyloxybenzyl 3-(4-fluorophenoxy)-2,2-dimethylcyclopropanecarboxylate, and m-(o-fluorophenoxy)benzyl 3-(4-fluorophenoxy)-2,2-dimethylcyclopropanecarboxylate.

In the same manner, m-(p-fluorophenoxy)benzyl 3-(4-fluorophenoxy)-2,2-dimethylcyclopropanecarboxylate is produced from 3-(4-fluorophenoxy)-2,2-dimethylcyclopropanecarboxylic acid and m-(p-fluorophenoxy)-benzyl bromide.

EXAMPLE 12

To a solution of 3.92 g (20 mmol) of phenylthiomethyltrimethylsilane in 10 ml THF at 0° is added 20 ml n-butyllithium in hexane. The resulting yellow solution is stirred for 15 min at 0°, and a solution of 1.44 g (20 mmol) of 2-methyl-1-propanal in 5 ml THF is added. The reaction mixture is stirred for 15 min at 0°, then for 2 hr at 25°. Brine (15 ml) is added and the product extracted with ether. The organic layer is dried over calcium sulfate, filtered and the solvent is removed under vacuum to give 2-methyl-1-propenyl phenyl sulfide, which is purified by distillation under vacuum.

Alternately, 2-methyl-1-propenyl phenyl sulfide can be made by the method wherein a mixture of 2-methyl-1-propanal (0.37 g, 5.1 mmol), benzenethiol (0.61 g, 5.5 mmol) and triethylamine (0.55 g, 5.5 mmol) in 50 ml of 1,2-dimethoxyethane is added dropwise into a vigorously stirred solution of titanium tetrachloride (1.89 g, 10 mmol) in 40 ml of 1,2-dimethoxyethane under an argon atmosphere at RT. After stirring for 2 days, the product is worked up in the usual way to yield 2-methyl-1-propenyl phenyl sulfide.

A third synthesis of the above product is described by Cohen et al., *J. Org. Chem.* 40, 812 (1975).

EXAMPLE 13

To a mixture of 1.94 g (11.8 mmol) of 2-methyl-1-propenyl phenyl sulfide, 200 mg anhydrous cupric sulfate and 10 ml cyclohexane heated under reflux is added, dropwise and with stirring over a 7 hr period, a solution of 6.58 g (58 mmol) of ethyl diazoacetate in 40 ml cyclohexane. After addition is complete, refluxing and stirring is continued for an additional 2 hr, and then the reaction mixture is filtered, dried and solvent is removed in vacuo to give ethyl 3-phenylthio-2,2-dimethylcyclopropanecarboxylate.

Alternately, when no catalyst is used, the reaction is carried out at a higher temperature (approx. 150°) for thermal decomposition. Xylene is heated to reflux and a mixture of 2-methyl-1-propenyl phenyl sulfide and ethyl diazoacetate is added dropwise over 2 hr. Reflux is continued an additional 1 hr or until nitrogen evolution has ceased. The reaction is then filtered, dried and solvent is removed, giving ethyl 3-phenylthio-2,2-dimethylcyclopropanecarboxylate.

Using the method of Example 3, the above product is hydrolyzed to 3-phenylthio-2,2-dimethylcyclopropanecarboxylic acid, which is then reacted with m-phenoxybenzyl bromide to yield m-phenoxybenzyl 3-phenylthio-2,2-dimethylcyclopropanecarboxylate.

EXAMPLE 14

A solution of 5.77 mmol of ethyl propiolate in 20 ml ethyl ether is treated with 5.77 mmol 2-chlorophenol and 0.4 ml triethylamine (added slowly and with stirring). The reaction mixture is stirred overnight at RT, after which the solvent is removed under vacuum to yield ethyl 3-phenoxy-2-propenoate.

The mixture of 20.9 g (113 mmol) sodium trichloroacetate, 15.4 g (80 mmol) ethyl 3-phenoxy-2-propenoate and 50 ml dry 1,2-dimethoxyethane is heated under reflux for 10 hr, under nitrogen. The mixture is filtered and solvent removed. The residue is purified by chromatography on silica gel, giving ethyl 3-phenoxy-2,2-dichlorocyclopropanecarboxylate, which is then hydrolyzed, as in Example 3, to give the corresponding carboxylic acid.

The carboxylic acid is reacted with each of m-phenoxybenzyl bromide and α-cyano-m-phenoxybenzyl methanesulfonate to yield, respectively, m-phenoxybenzyl 3-phenoxy-2,2-dichlorocyclopropanecarboxylate and α-cyano-m-phenoxybenzyl 3-phenoxy-2,2-dichlorocyclopropanecarboxylate.

EXAMPLE 15

A solution of 2.45 g (24.54 mmol) methyl propiolate and 20 ml ether is treated with 2.7 g (24.54 mmol) benzenethiol with 4 drops triethylamine in 25 ml ether over 15 min at 20°. After stirring for 24 hr, the reaction mixture is rotoevaporated to yield methyl 3-phenylthio-2-propenoate.

Freshly distilled ethyl trichloroacetate (164.8 g, 0.86 mmol) is added all at once to a cold (−50°) stirred mixture of dry methyl 3-phenylthio-2-propenoate (155.4 g, 0.8 mol), dry olefin-free pentane (600 ml) and sodium methoxide (50 g, 0.92 mol). The cold mixture is allowed to stir under nitrogen at −50° for 4 hr and is then warmed slowly to RT over a period of 24 hr. Ether and water are added, and the organic layer is separated, washed with water, dried over calcium sulfate and solvent is removed under vacuum. The residue is purified by chromatography on silica gel, giving methyl 3-phenylthio-2,2-dichlorocyclopropanecarboxylate.

The methyl 3-phenylthio-2,2-dichlorocyclopropanecarboxylate is hydrolyzed, following, for example, Example 3 method, and the resulting carboxylic acid is reacted with each of m-phenoxybenzyl bromide and α-cyano-m-phenoxybenzyl methanesulfonate to yield, respectively, m-phenoxybenzyl 3-phenylthio-2,2-dichlorocyclopropanecarboxylate and α-cyano m-phenoxybenzyl 3-phenylthio-2,2-dichlorocyclopropanecarboxylate.

EXAMPLE 16

Following the method of Example 14, methyl propiolate and 4-chlorophenol are reacted to yield methyl 3-(4-chlorophenoxy)-2-propenoate.

A mixture of methyl 3-(4-chlorophenoxy)-2-propenoate (30 mmol), phenyl(bromodichloromethyl)mercury (30 mmol) and 50 ml benzene are heated under reflux, with stirring, for 4 hr, followed by TLC of the product. The mixture is then filtered and the solvent removed, giving methyl 3-(4-chlorophenoxy)-2,2-dichlorocyclopropanecarboxylate, which is then hydrolyzed and reacted with m-phenoxybenzyl bromide to give m-phenoxybenzyl 3-(4-chlorophenoxy)-2,2-dichlorocyclopropanecarboxylate.

Similarly, the methyl 3-(4-chlorophenoxy)-2-propenoate is reacted with each of phenyl(tribromomethyl)mercury (with benzene, refluxing 4 hr), phenyl(bromochloroiodomethyl)mercury (with benzene and refluxing 15 min), and phenyl(dichlorofluoromethyl)mercury (with benzene and refluxing 48 hr) to give, respectively, methyl 3-(4-chlorophenoxy)-2,2-dibromocyclopropanecarboxylate, methyl 3-(4-chlorophenoxy)-2-bromo-2-chlorocyclopropanecarboxylate, and methyl 3-(4-chlorophenoxy)-2-chloro-2-fluorocyclopropanecarboxylate.

Each of these products is hydrolyzed and reacted with m-phenoxybenzyl bromide, yielding, respectively, the m-phenoxybenzyl ester of 3-(4-chlorophenoxy)-2,2-dibromocyclopropanecarboxylate, 3-(4-chlorophenoxy)-2-bromo-2-chlorocyclopropanecarboxylate, and 3-(4-clorophenoxy)-2-chloro-2-fluorocyclopropanecarboxylate.

EXAMPLE 17

Using Example 15 procedures, ethyl propiolate and 4-fluorobenzenethiol are reacted, yielding ethyl 3-(4-fluorophenylthio)-2-propenoate. Three equiv. of this is then combined with 1 equiv. of phenyl(trifluoromethyl)mercury and 3 equiv. of dry powdered sodium iodide. This mixture is refluxed in benzene for 15-20 hr, then filtered and solvent is removed to give ethyl 3-(4-fluorophenylthio)-2,2-difluorocyclopropanecarboxylate.

Ethyl 3-(4-fluorophenylthio)-2-propenoate can also be combined with phenyl(dibromofluoromethyl)mercury, in 1:1 ratio, and heated at 80°, with stirring for 30 min, to give ethyl 3-(4-fluorophenylthio)-2-bromo-2-fluorocyclopropanecarboxylate.

Each of ethyl 3-(4-fluorophenylthio)-2,2-difluorocyclopropanecarboxylate and ethyl 3-(4-fluorophenylthio)-2-bromo-2-fluorocyclopropanecarboxylate is hydrolyzed and reacted with m-phenoxybenzyl bromide to yield, respectively, m-phenoxybenzyl 3-(4-fluorophenylthio)-2,2-difluorocyclopropanecarboxylate and m-phenoxybenzyl 3-(4-fluorophenylthio)-2-bromo-2-fluorocyclopropanecarboxylate.

Two groups of 10 each of 0-24 hr III instar *Heliothis virescens* larvae are treated with 1 ul of compound 2a [believed to be the cis isomer of α-cyano-m-phenoxybenzyl 3-(4-chlorophenoxy)-2,2-dimethylcyclopropanecarboxylate] in acetone at three different concentrations by application to the dorsum of the thorax. Two groups of 10 each are treated identically with 1 ul acetone as controls. Larvae are held individually in 30 ml plastic cups provided with artificial medium for 72 hr at 25° and 16 hr photoperiod. After 72 hr, the number of dead is calculated as a percentage of the total number originally treated and then corrected for any mortality in the control groups using Abbott's formula. The $LC_{50}$ of the compound was less than 0.1 ug/animal.

Two groups of 15 each of 72-hour-old adult female *Musca domestica* L. are anesthetized with ether vapor. These are then treated with 1 ul of either compound 2a or compound 2b [the cis or trans isomer of α-cyano-m-phenoxybenzyl 3-(4-chlorophenoxy)-2,2-dimethylcyclopropanecarboxylate] diluted to three different concentrations in a acetone applied to the dorsal surface of the prothorax. They are held in an assay container with milk-saturated cotton at 25°, 16hr photoperiod for 24hr. The effect is stated as the number dead calculated as a percentage of the total treated, corrected for any control mortality using Abbott's formula. Each compound gave an $LC_{50}$ of less than 0.5 ug/animal.

Into a mixture of 45 mg of wettable powder [Attaclay (60%), Marosperse N-22 (26.7%) and Igepon T-77 (13.3%)] and 0.5 ml of water containing the compound 2a at three different concentrations is dipped 15 fed tick numphs (Ornithodoros nymph I). The treated nymphs are maintained on filter paper for 7 days at 28°, 64% humidity, 16 hr photoperiod and then observed. Correction is made for any mortality in the control using Abbott's formula. The $LC_{50}$ of the compound was less than 5 ppm.

Twenty 0-24 hr I instar larvae of *Manduca sexta* are placed in individual containers with artificial food treated with either the compound [m-phenoxybenzyl 3-(2,2,2-trifluoroethoxy)-2,2-dimethylcyclopropanecarboxylate] or the compound [m-phenoxybenzyl 3-(4-methylphenoxy)-2,2-dimethylcyclopropanecarboxylate] (0.5 ml acetone and 0.5 ml water, containing the compound, into 200 ml food) at three different concentrations. The animals are held, at 27° and 16 hr photoperiod, until they reach the V instar. The effect is stated as the number dead calculated as a percentage of the total, corrected for any control mortality using Abbott's formula. The $LC_{50}$ of each compound was less than 5 ppm.

Twenty 4-day-old adult alfalfa weevils (*Hypera postica*) are treated with 1 ul of either compound 2a or compound 2b in acetone at three different concentrations by application to the dorsum of the thorax. They are held for 7 days (no food is required) at 25° and 16 hr photoperiod. The number dead is calculated as a percentage of the total and corrected for any control mortality using Abbott's formula. Each compound had an $LC_{50}$ of less than 0.5 ug/animal.

Compound 2b was applied to *Heliothis virescens* larvae using the method described above and exhibited an $LC_{50}$ of less than 0.2 ug/animal.

What is claimed is:

1. A compound of the formula:

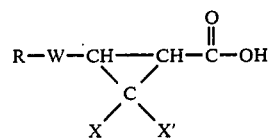

wherein,
W is oxygen or sulfur;
X is lower alkyl or halogen;
X' is hydrogen, lower alkyl or halogen;
R is lower haloalkyl, lower alkenyl, or lower haloalkenyl; and the inorganic salts thereof and lower alkyl esters thereof.

2. A compound according to claim 1 wherein X is hydrogen or methyl, X' is methyl and R is lower haloalkyl.

3. A compound according to claim 2 wherein X is methyl and W is oxygen.

4. A compound according to claim 1 wherein X is hydrogen or methyl, X' is methyl and R is lower alkenyl.

5. A compound according to claim 4 wherein X is methyl and W is oxygen.

6. A compound according to claim 1 wherein X is hydrogen or methyl, X' is methyl and R is lower haloalkenyl.

7. A compound according to claim 6 wherein X is methyl and W is oxygen.

8. The compound, 3-(2,2,2-trifluoroethoxy)-2,2-dimethylcyclopropanecarboxylic acid, according to claim 3.

9. The compound, 3-(but-2-enoxy)-2,2-dimethylcyclopropanecarboxylic acid, according to claim 5.

10. The compound, 3-(3-fluoropropenoxy)-2,2-dimethylcyclopropanecarboxylic acid, according to claim 7.

11. The compound, 3-(4-chloro-3-fluorobut-2-enoxy)-2,2-dimethylcyclopropanecarboxylic acid, according to claim 7.

* * * * *